(12) United States Patent
Leone (10) Patent No.: US 10,488,361 B2
(45) Date of Patent: Nov. 26, 2019

(54) CAPACITIVE AUTOCODING

(71) Applicant: Trividia Health, Inc., Fort Lauderdale, FL (US)

(72) Inventor: Steven V. Leone, Lake Worth, FL (US)

(73) Assignee: Trividia Health, Inc., Fort Lauderdale, FL (US)

( * ) Notice: Subject to any disclaimer, the term of this patent is extended or adjusted under 35 U.S.C. 154(b) by 155 days.

(21) Appl. No.: 15/686,429

(22) Filed: Aug. 25, 2017

(65) Prior Publication Data

US 2018/0059043 A1    Mar. 1, 2018

Related U.S. Application Data

(60) Provisional application No. 62/379,829, filed on Aug. 26, 2016.

(51) Int. Cl.
    *G01N 27/327*    (2006.01)
    *C12Q 1/00*      (2006.01)
    *G06K 7/10*      (2006.01)

(52) U.S. Cl.
    CPC ......... *G01N 27/3274* (2013.01); *C12Q 1/006* (2013.01); *G01N 27/3272* (2013.01); *G06K 7/10009* (2013.01)

(58) Field of Classification Search
    CPC .......................................... G01N 27/327–3278
    USPC ..... 204/403.01–403.15; 205/777.5–778, 792
    See application file for complete search history.

(56) References Cited

U.S. PATENT DOCUMENTS

| | | | |
|---|---|---|---|
| 5,651,025 A | 7/1997 | May | |
| 2007/0110615 A1* | 5/2007 | Neel | G01N 33/48771 422/400 |
| 2009/0042306 A1* | 2/2009 | Reynolds | G01N 33/48771 436/46 |
| 2015/0136853 A1 | 5/2015 | Palmer et al. | |
| 2015/0097549 A1 | 8/2015 | Welsh et al. | |
| 2016/0077039 A1 | 3/2016 | Modzelewski et al. | |

OTHER PUBLICATIONS

International Search Report for corresponding International Application No. PCT/US17/48593, dated Nov. 9, 2017.

\* cited by examiner

*Primary Examiner* — Bach T Dinh
(74) *Attorney, Agent, or Firm* — Greenberg Traurig, LLP; David J. Dykeman; Roman Fayerberg (57) ABSTRACT

A capacitive autocoding circuit is provided herein. A test strip may include an embedded code comprising one or more individually electrically isolated contacting pads associated with one of a plurality of predefined capacitive states. The respective capacitive states associated with each of the contacting pads together form a capacitive state sequence such that when the test strip is inserted into a diagnostic meter the sequence is read to identify data particular to the capacitive sequence and the test strip.

18 Claims, 9 Drawing Sheets

FIG. 8

CAPACITIVE AUTOCODING

This application claims priority to U.S. Provisional Patent Application Ser. No. 62/379,829, filed Aug. 26, 2016, the entire contents of which are incorporated herein by reference.

TECHNICAL FIELD

The present invention relates to electrochemical sensors and, more particularly, to systems and methods for electrochemically sensing a particular constituent within a fluid through the use of diagnostic test strips including regions having a predetermined electrical property useful in identifying a test strip.

BACKGROUND

Many industries have a commercial need to monitor the concentration of particular constituents in a fluid. The oil refining industry, wineries, and the dairy industry are examples of industries where fluid testing is routine. In the health care field, people such as diabetics, for example, have a need to monitor a particular constituent within their bodily fluids. A number of systems are available that allow people to test a body fluid, such as, blood, urine, or saliva, to conveniently monitor the level of a particular fluid constituent, such as, for example, cholesterol, proteins, and glucose. Patients suffering from diabetes, a disorder of the pancreas where insufficient insulin production prevents the proper digestion of sugar, have a need to carefully monitor their blood glucose levels on a daily basis. A number of systems that allow people to conveniently monitor their blood glucose levels are available. Such systems typically include a test strip where the user applies a blood sample and a meter that "reads" the test strip to determine the glucose level in the blood sample.

Among the various technologies available for measuring blood glucose levels, electrochemical technologies are particularly desirable because only a very small blood sample may be needed to perform the measurement. In amperometric electrochemical-based systems, the test strip typically includes a sample chamber that contains reagents, such as glucose oxidase and a mediator, and electrodes. When the user applies a blood sample to the sample chamber, the reagents react with the glucose, and the meter applies a voltage to the electrodes to cause a redox reaction. The meter measures the resulting current and calculates the glucose level based on the current. Other systems based on coulometry or voltametry are also known.

Because the test strip includes a biological reagent, every strip manufactured is not reproducible with the exact same sensitivity. Therefore, test strips are manufactured in distinct lots and data particular to that lot is often used as a signal by the meter's microprocessor to assist in accurately performing the meter calculation. The data is used to help accurately correlate the measured current with the actual glucose concentration. For example, the data could represent a numeric code that "signals" the meter's microprocessor to access and utilize a specific set of stored calibration values from an on-board memory device during calculation.

In past systems, the code particular to a specific lot of strips has been inputted into the meter manually by the user, or connected through some type of memory device (such as a ROM chip) packaged along with test strips from a single manufacturing lot. This step of manual input, or connection by the user, adds to the risk of improperly inputting the wrong code data. Such errors can lead to inaccurate measurements and an improper recording of the patient's history. Past systems have also included bar-code readable information incorporated onto individual strips. Individually imprinting a particular bar-code on each strip adds significant manufacturing costs to the strip production and requires the additional expense of a bar-code reader incorporated within the meter in order to obtain the information.

SUMMARY

Embodiments of the application are directed to a diagnostic test strip, a diagnostic test strip meter, and a method of making a plurality of test strips that can provide accurate measurements of concentration levels in a body fluid, such as blood, that can be critical to the long-term health of many users. As a result, there is a need for a high level of reliability in the meters and test strips used to measure concentration levels in fluids. Thus, diagnostic test strips provided herein include a cost effective auto-calibration system that more reliably and more accurately provides an autocode for individual test strips.

In some embodiments, a test strip is provided. The test strip includes an electrically insulating layer, and a conductive pattern formed on the at least one insulating layer including at least one electrode disposed on the at least one insulating layer at a proximal region of the strip. The one or more electrical strip contacts can be disposed on the at least one insulating layer at a distal region of the test strip. Conductive traces electrically connecting the electrodes to at least one of the electrical strip contacts. The test strip also includes a reagent layer contacting at least a portion of at least one electrode, and an embedded code comprising one or more individually electrically isolated contacting pads provided distal to the electrical strip contacts. The contacting pads are associated with one of a plurality of predefined capacitive states. The respective capacitive states associated with each of the contacting pads together form a capacitive state sequence such that when the test strip is inserted into a diagnostic meter the sequence is read to identify data particular to the capacitive sequence and the test strip.

In some embodiments, a method of coding a test strip is provided. The method includes providing a test strip having one or more individually electrically isolated contacting pads, reading a predetermined capacitive state related to the one or more contacting pads, and identifying data particular to the test strip based on a capacitive state sequence formed from the respective capacitive states of each of the contacting pads.

In some embodiments, a method of making a plurality of test strips is provided. The method includes forming a plurality of test strip structures on one sheet. Each of the test strip structures can include an electrically insulating layer, and a conductive pattern formed on the at least one insulating layer including at least one electrode disposed on the at least one insulating layer at a proximal region of the strip. One or more electrical strip contacts can be disposed on the at least one insulating layer at a distal region of the test strip. Conductive traces electrically connect the electrodes to at least one of the electrical strip contacts. The test strip also includes a reagent layer contacting at least a portion of at least one electrode, and an embedded code comprising one or more individually electrically isolated contacting pads provided distal to the electrical strip contacts. The contacting pads are associated with one of a plurality of predefined capacitive states. The respective capacitive states associated with each of the contacting pads together form a capacitive state sequence such that when the test strip is inserted into a diagnostic meter the sequence is read to identify data particular to the capacitive sequence and the test strip. The method includes separating the test strip structures into the plurality of test strips.

In some embodiments, the test strip structures can include an additional conductive pattern formed on the insulating layer on a side opposite from that including the electrical strip contacts. The additional conductive pattern can include a second plurality of electrical strip contacts and at least one additional contact pad electrically connected to one or more capacitors configured in one of the plurality of predefined capacitive states to form a second capacitive state sequence to identify additional data particular to the test strip.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Reference will now be made in detail to the exemplary embodiments of the invention, examples of which are illustrated in the accompanying drawings. Wherever possible, the same reference numbers will be used throughout the drawings to refer to the same or like parts.

According to exemplary embodiments, a system is provided for measuring a body fluid constituent including a test strip and a meter. In some embodiments, an individual test strip can also include an embedded code relating to data associated with a lot of test strips, or data particular to that individual strip. The embedded information presents data readable by the meter signaling the meter's microprocessor to access and utilize a specific set of stored calibration parameters particular to test strips from a manufacturing lot to which the individual strip belongs, or to an individual test strip. The system can also include a check strip that the user may insert into the meter to check that the instrument is electrically calibrated and functioning properly. For purposes of this disclosure, "distal" refers to the portion of a test strip further from the device operator during normal use and "proximal" refers to the portion closer to the device operator during normal use.

The test strip can include a sample chamber for receiving a user's fluid sample, such as, for example, a blood sample. The sample chamber and test strip of the present specification can be formed using materials and methods described in commonly owned U.S. Pat. No. 6,743,635 filed on Nov. 1, 2002 and entitled "System and Methods for Blood Glucose Sensing", which is hereby incorporated by reference in its entirety. Accordingly, the sample chamber can include a first opening in the proximal end of the test strip and a second opening for venting the sample chamber. The sample chamber can be dimensioned so as to be able to draw the blood sample in through the first opening, and to hold the blood sample in the sample chamber, by capillary action. The test strip can include a tapered section that is narrowest at the proximal end, or can include other indicia in order to make it easier for the user to locate the first opening and apply the blood sample.

A working electrode and counter electrode can be disposed in the sample chamber optionally along with fill-detect electrodes. A reagent layer is disposed in the sample chamber and preferably contacts at least the working electrode. The reagent layer may include an enzyme, such as glucose oxidase, and a mediator, such as potassium ferricyanide or ruthenium hexamine. The test strip has, near its distal end, a plurality of electrical strip contacts that are electrically connected to the electrodes via conductive traces. In addition, the test strip may also include a plurality of contact pads near the distal end of the strip. The plurality of contact pads can each be electrically connected to one or more capacitors, where the capacitors are each in one of a plurality of capacitive states such that they provide, when the strip is inserted into the meter, a distinctly discernable capacitive state sequence (also referred to herein as a code) readable by the meter. As noted above, the readable capacitive state sequence can be read as a signal to access data, such as calibration coefficients, from an on-board memory unit in the meter related to test strips from that lot, or even information corresponding to individual test strips.

The capacitive states can include, for example, one or more predefined capacitance values. The capacitive states may be varied from strip to strip or from strip lot to strip lot by using capacitance values or combinations of capacitance values on the capacitors of each strip or on each strip lot. For example, a certain combination of capacitance values can define the capacitive state sequence for a test strip. This pattern can be varied from strip to strip or from strip lot to strip lot to allow the test strip to be associated with various characteristics when read by the test strip meter. The pattern can be varied by altering the capacitive state of one or more of the capacitors.

The meter may be battery powered and may stay in a low-power sleep mode when not in use in order to save power. When the test strip is inserted into the meter, the plurality of electrical strip contacts and the contact pads on the test strip contact corresponding electrical contacts in the meter. The contact pads may bridge a pair of electrical contacts in the meter, causing a current to flow through at least a portion of the contact pads. The current flow through the contact pads causes the meter to wake up and enter an active mode. The meter also reads the code information provided by the capacitive state sequence associated with the contact pads and can then identify, for example, the particular test to be performed, or a confirmation of proper operating status. In addition, the meter can also identify the inserted strip as either a test strip or a check strip based on the particular code information. If the meter detects a check strip, it performs a check strip sequence. If the meter detects a test strip, it performs a test strip sequence.

In the test strip sequence, the meter validates the working electrode, counter electrode, and, if included, the fill-detect electrodes, by confirming that there are no low-impedance paths between any of these electrodes. If the electrodes are valid, the meter indicates to the user that sample may be applied to the test strip. The meter then applies a drop-detect voltage between the working and counter electrodes and detects a fluid sample, for example, a blood sample, by detecting a current flow between the working and counter electrodes (i.e., a current flow through the blood sample as it bridges the working and counter electrodes). To detect that an adequate sample is present in the sample chamber and that the blood sample has traversed the reagent layer and mixed with the chemical constituents in the reagent layer, the meter may apply a fill-detect voltage between the fill-detect electrodes and measure any resulting current flowing between the fill-detect electrodes. If this resulting current reaches a sufficient level within a predetermined period of time, the meter indicates to the user that adequate sample is present and has mixed with the reagent layer.

In one embodiment, the test strip meter comprises a decoder for decoding a predetermined electrical property, e.g. a capacitive state sequence from the test strips as information. The decoder operates with, or is a part of, a microprocessor.

The meter can be programmed to wait for a predetermined period of time after initially detecting the blood sample, to allow the blood sample to react with the reagent layer or can immediately begin taking readings in sequence. During a fluid measurement period, the meter applies an assay voltage between the working and counter electrodes and takes one or more measurements of the resulting current flowing between the working and counter electrodes. The assay voltage is near the redox potential of the chemistry in the reagent layer, and the resulting current is related to the concentration of the particular constituent measured, such as, for example, the glucose level in a blood sample.

In one example, the reagent layer may react with glucose in the blood sample in order to determine the particular glucose concentration. In one example, glucose oxidase is used in the reagent layer. The recitation of glucose oxidase is intended as an example only and other materials can be used without departing from the scope of the invention. Other possible mediators include, but are not limited to, ruthenium and osmium. During a sample test, the glucose oxidase initiates a reaction that oxidizes the glucose to gluconic acid and reduces the ferricyanide to ferrocyanide. When an appropriate voltage is applied to a working electrode, relative to a counter electrode, the ferrocyanide is oxidized to ferricyanide, thereby generating a current that is related to the glucose concentration in the blood sample. The meter then calculates the glucose level based on the measured current and on calibration data that the meter has been signaled to access by the code data read from the second plurality of electrical contacts associated with the test strip. The meter then displays the calculated glucose level to the user. Each of the above-described components and their interconnection will now be described.

Figure 1:
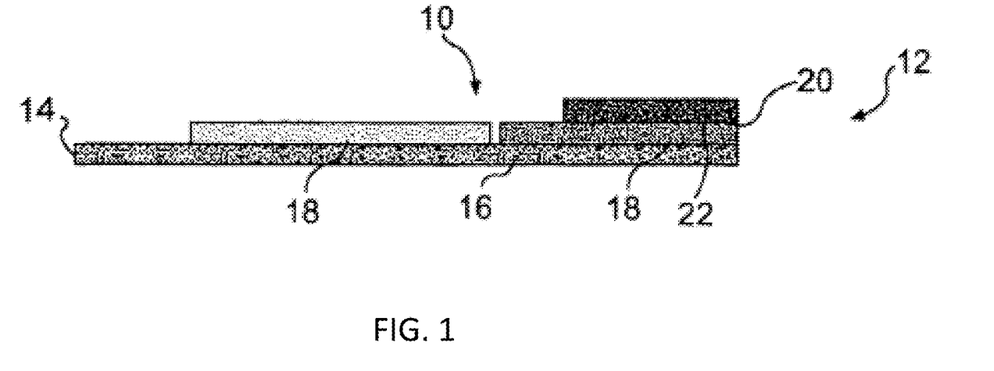
FIG. 1 is a general cross-sectional view of a test strip in accordance with various embodiments.

FIG. 1 illustrates a general cross-sectional view of an embodiment of a test strip 10. The test strip 10 includes a proximal connecting end 12, a distal end 14, and is formed with a base layer 16 extending along the entire length of test strip 10. The base layer 16 can be composed of an electrically insulating material and has a thickness sufficient to provide structural support to test strip 10. For purposes of this application, an insulating material (e.g. an insulating layer, coating, ink, or substrate etc.) comprises any material in which electrons or ions cannot be moved easily, hence preventing the flow of electric current. Accordingly, an element can be said to be insulated when it is separated from other conducting surfaces by a dielectric substance or air space permanently offering a high resistance to the passage of current and to disruptive discharge through the substance or space. By contrast, for purposes of this application, a resistive element, is one that introduces an increased level of impedance into a circuit that reduces (but does not necessarily prevent) the flow of electric current. The base layer 16, for example, can be polyester that is about 0.014 inches thick, although other sizes can be used depending on the particular application and manufacturing method. Disposed on the base layer 16 is a conductive pattern (not shown) with a predetermined resistance.

The conductive pattern includes a plurality of electrodes disposed on base layer 16 near proximal end 12, a plurality of electrical strip contacts disposed on base layer 16 near distal end 14, and a plurality of conductive traces electrically connecting the electrodes to the plurality of electrical strip contacts. For purposes of this application, the noun "contact" denotes an area intended for mechanical engagement with another corresponding "contact" irrespective of whether an electric circuit is completed, or passes through the particular area.

In some embodiments, the plurality of electrodes may include a working electrode, a counter electrode, and fill-detect electrodes. The conductive pattern can be applied by applying a conductive material onto the base layer 16. The conductive pattern can be applied to the top side of the strip, the bottom side of the strip, or a combination of both. The electrode material can be provided by thin film vacuum sputtering of a conductive material (e.g. Gold) and a semiconductive material (e.g. Indium Zinc Oxide) onto the base layer 16. The resulting electrode layer can then be further patterned according to the specific application by forming particular conductive regions/pathways through a laser ablation process. Alternative materials and methods for providing a conductive pattern in addition to screen printing can be employed.

A dielectric insulating layer 18 can be formed over the conductive pattern along a portion of the test strip between the measuring electrodes and the plurality of electrical strip contacts in order to prevent scratching, and other damage, to the electrical connection. As seen in FIG. 1, the proximal end 12 of the test strip 10 includes a sample receiving location, such as a sample chamber 20 configured to receive a patient's fluid sample, as described above. The sample chamber 20 can be formed in part through a slot formed between a cover 22 and the underlying measuring electrodes formed on the base layer 16. The relative position of the measuring electrodes and the electrical strip contacts form a proximal electrode region 24 at one end of strip 10 and a distal strip contact region 26 at the other end.

Figure 2:
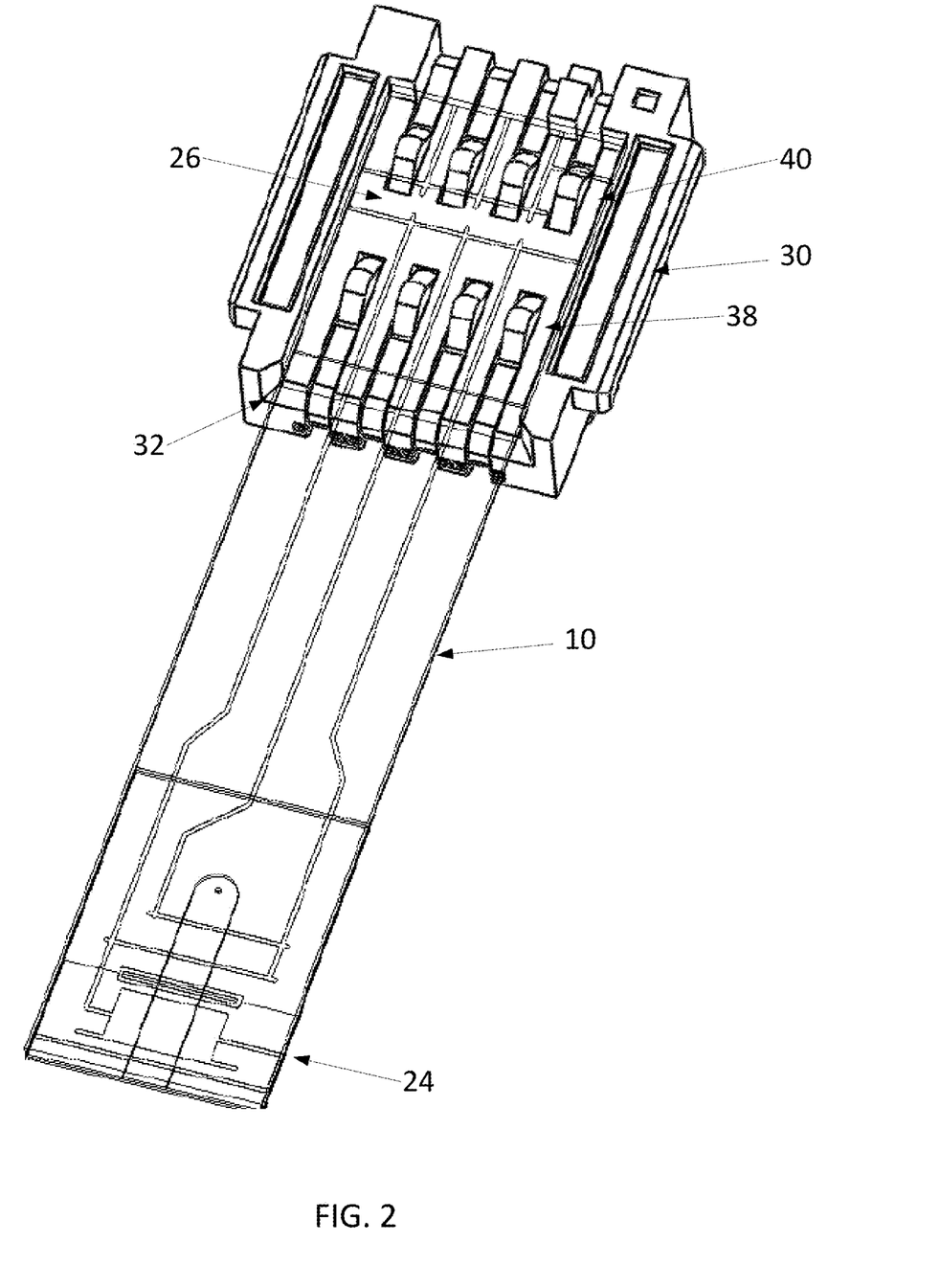
FIG. 2 is a top perspective view of a test strip inserted within a meter strip connector in accordance with various embodiments.

Referring to FIG. 2, a top perspective view of a test strip 10 inserted within a meter connector 30 is illustrated. As seen in FIG. 2, the test strip 10 includes a proximal electrode region 24, which contains the sample chamber and measuring electrodes described above. The proximal electrode region 24 can be formed to have a particular shape in order to distinguish to the user, the end receiving a fluid sample from distal strip contact region 26. The meter connector 30 includes channel 32 extending out to a flared opening for receiving the test strip 10.

Figure 3:
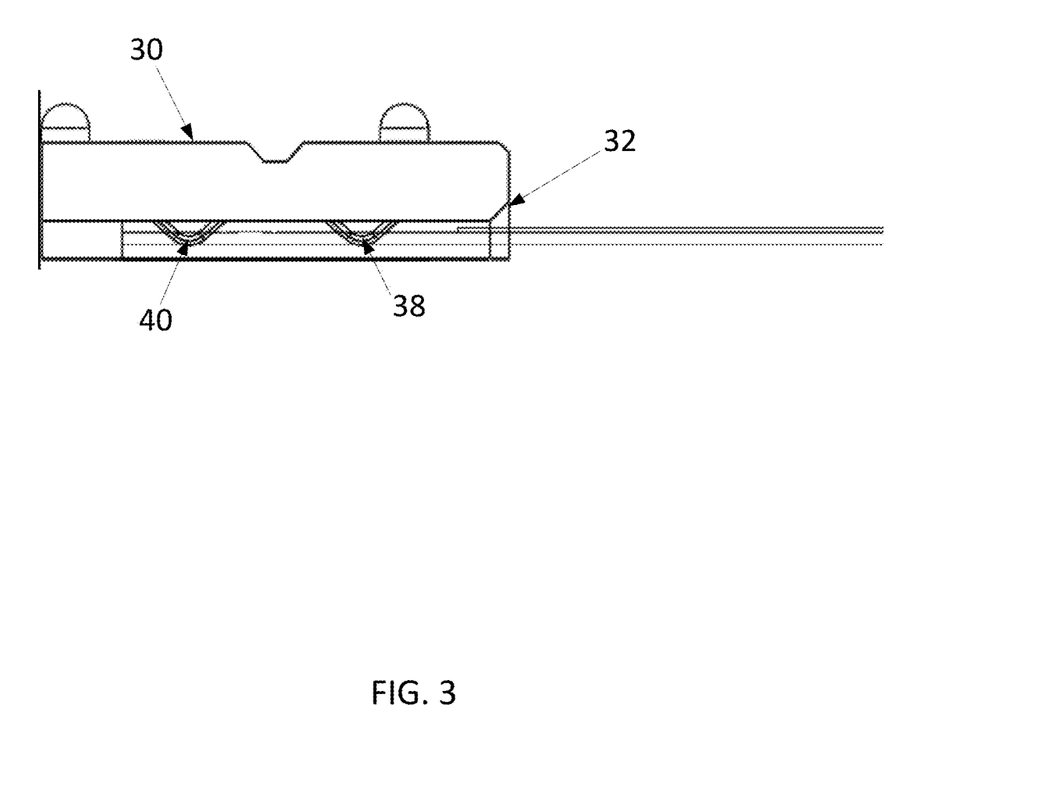
FIG. 3 is a general cross-sectional view of a test strip inserted within a meter strip connector in accordance with various embodiments.

The connector 30 further includes a first plurality of connector contacts 38, disposed closer to the proximal end of the connector 30, and a second plurality of connector contacts 40 disposed closer to the distal end of the connector 30. As illustrated, the test strip 10 is inserted into the flared opening with the distal strip contact region 26 extending first through the connector channel 32. With reference to FIG. 3, a general cross-sectional view of a test strip inserted within a meter strip connector 30 is illustrated. The channel 32 includes a proximal row of connectors comprising a first plurality of connector contacts 38. In addition, the channel 32 houses a distal row of connectors comprising a second plurality of connector contacts 40. The connector contacts 38, 40 are positioned within the channel 32 in order to make contact with distinct portions of the distal strip contact region 26 of the test strip 10, as will be described more fully below.

FIG. 3 is a general cross-sectional view of a test strip inserted within a meter strip connector 30 according to some embodiments of the invention. In some embodiments, the connector 30 contacts the test strip. In some embodiments, the connector contacts 38, 40 also make contact with the test strip 10.

Figure 4:
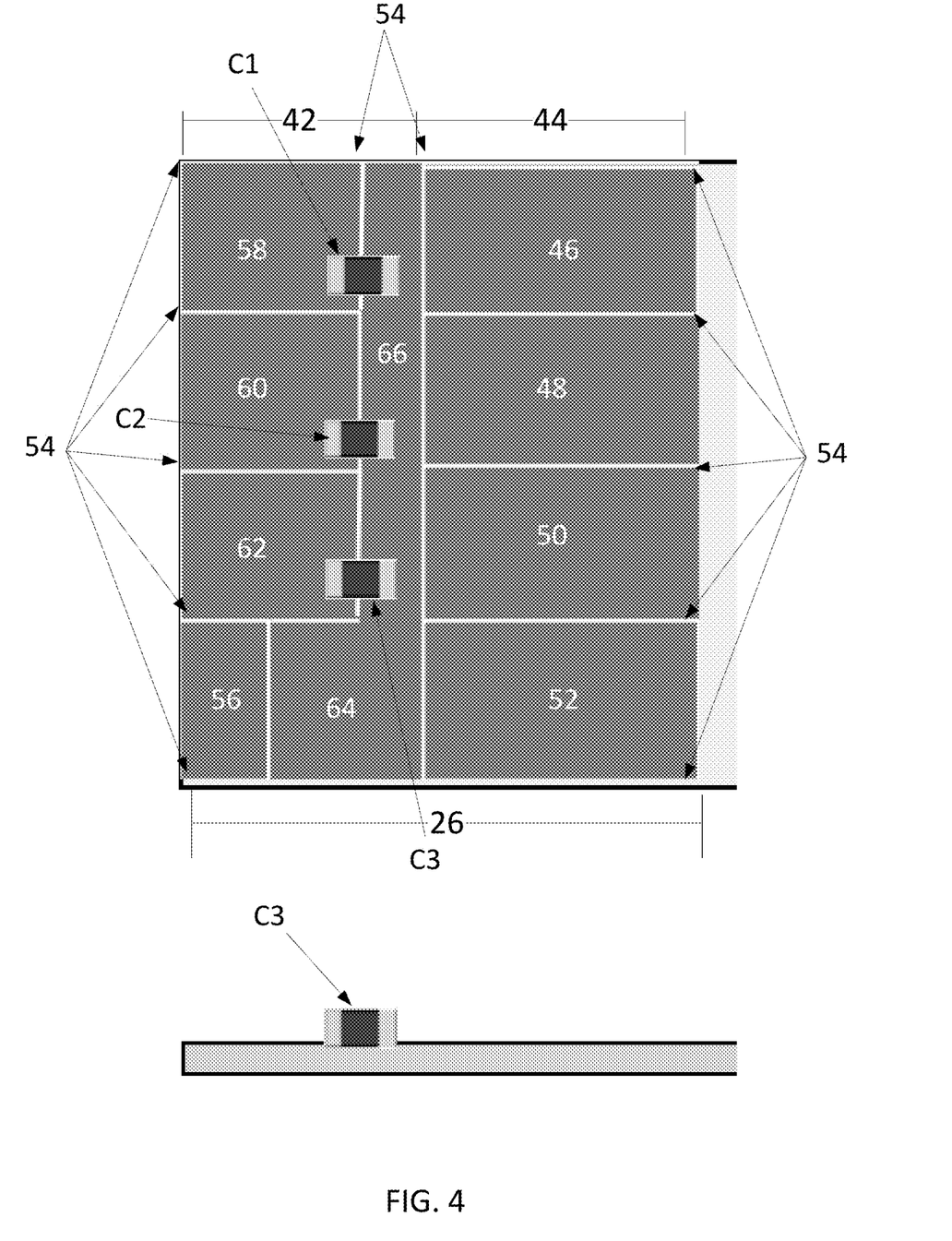
FIG. 4 is a top and side view illustrating a test strip having a distal portion including discrete capacitors in accordance with various embodiments.

FIG. 4 is a top and side view of a test strip 10 illustrating the distal strip contact region 26. The conductive pattern formed on the base layer 16 extends along the test strip 10 to include the distal strip contact region 26. As illustrated in FIG. 4, the distal strip contact region 26 is divided to form two distinct conductive regions 42, 44 respectively. However, the test strip 10 can comprise more than two distinct conductive regions. The conductive region 44 is divided into four columns forming a plurality of electrical strip contacts, labeled 46, 48, 50, 52 respectively. The plurality of electrical strip contacts 46, 48, 50, 52 are electrically connected to the plurality of measuring electrodes at the distal end of the test strip 10 as explained above. It should be understood that the four contacts 46, 48, 50, 52 are merely exemplary, and the system could include fewer or more electrical strip contacts corresponding to the number of measuring electrodes included in the system.

The first plurality of electrical strip contacts 46, 48, 50, 52 are divided, for example, through breaks 54 formed through the underlying conductive pattern in the test strip 10. These breaks 54 could be formed in the conductive pattern using a variety of techniques, including during printing, through a scribe process, laser ablated, or through a chemical/photo-etching type process. In addition, other processes of forming conductive breaks by removing a conductor in the test strip 10 can be used as would be apparent to one having ordinary skill in the art. Additional breaks 54 divide the conductive region 44 from the conductive region 42 within the distal strip contact region 26 with a common ground 66 therebetween and a further break 54 that separates the upper right-hand portion of the distal strip contact region 26 to form a notch region 56, as will be described more fully in detail below.

Figure 6A:
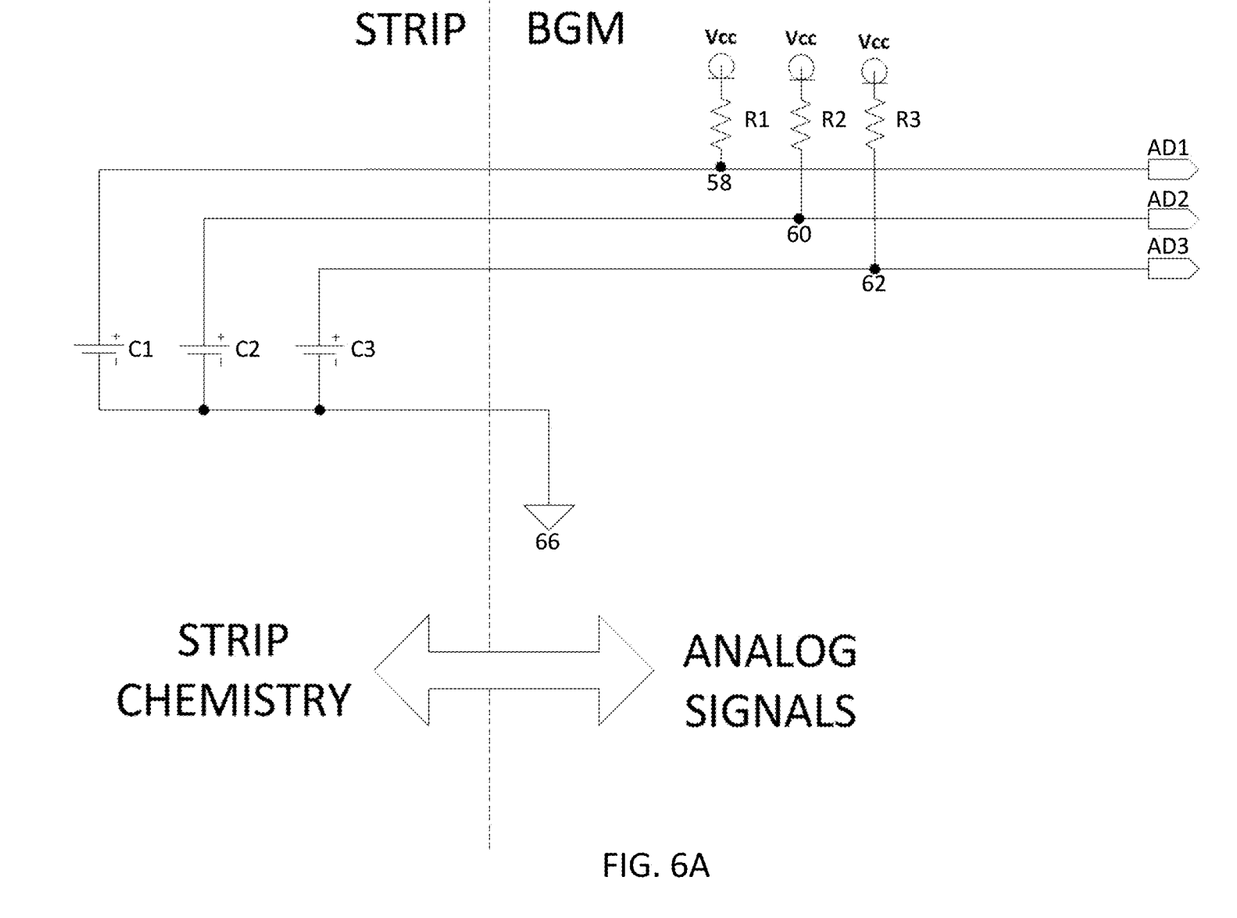
FIG. 6A is a simplified schematic diagram of the electrical connections between a meter and a plurality of capacitors of a test strip in accordance with various embodiments.
Figure 6B:
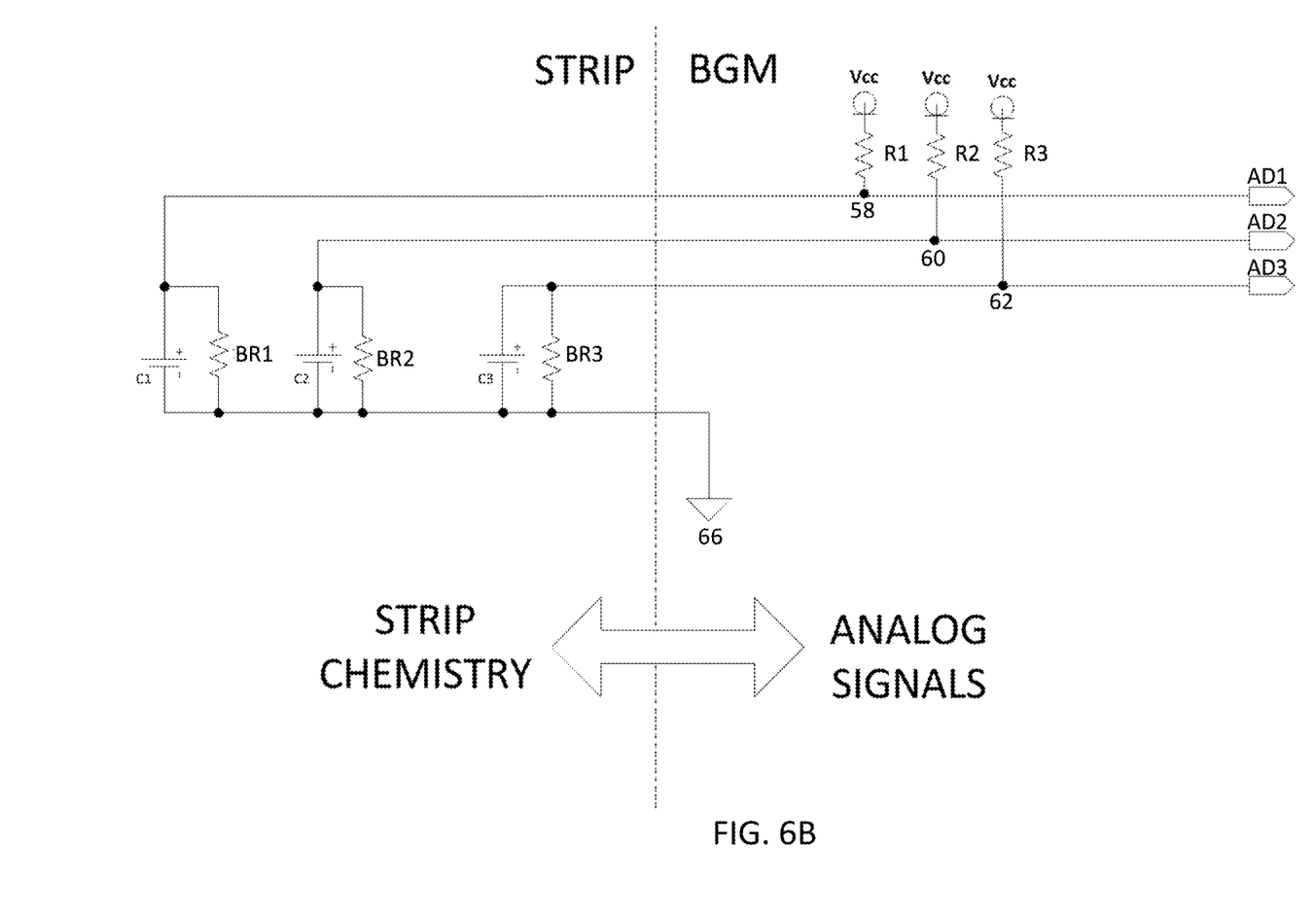
FIG. 6B is an alternative simplified schematic diagram of the electrical connections between a meter and a plurality of capacitors of a test strip connected to bleeder resistors in accordance with various embodiments.
Figure 7:
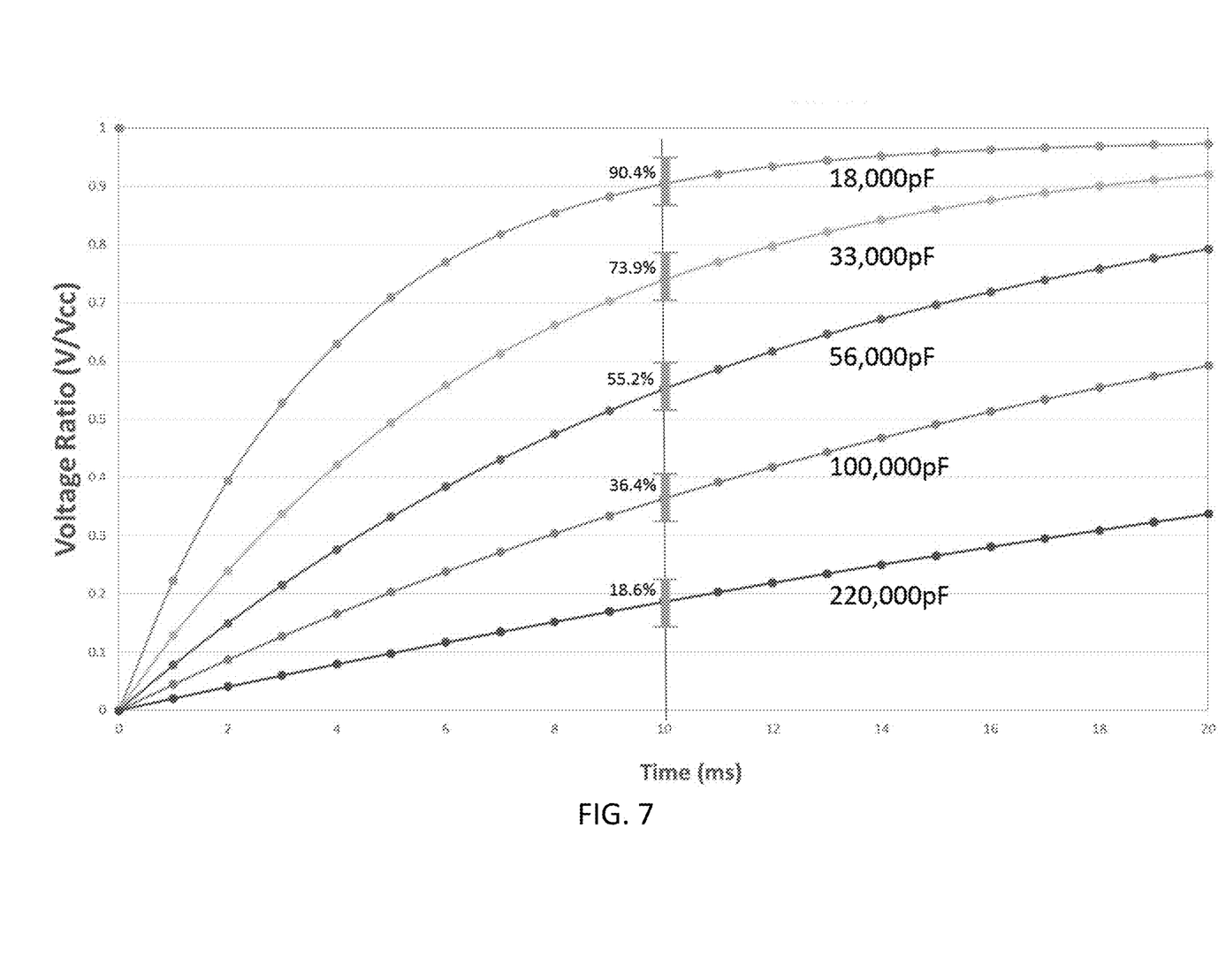
FIG. 7 is a graph showing voltage over time for each of a plurality of capacitive states in accordance with various embodiments.

FIG. 4 also illustrates the conductive region 42 divided into four distinct regions outlining a plurality of contact pads 58, 60, 62, 64 respectively. The contact pads 58, 60, 62, 64 as well as the ground 66 can be divided through the same process used to divide the plurality of the electrical strip contacts, 46, 48, 50, 52, described above. As shown in FIGS. 6A and 6B, one or more of the contact pads 58, 60, 62, 64 (e.g., 58, 60, 62 as shown in FIGS. 6A and 6B) is connected to at least one capacitor C1-C3, each capacitor C1-C3 being in one of a plurality of capacitive states (e.g., one of 18,000 pF, 33,000 pF, 56,000 pF, 100,000 pF, or 220,000 pF as shown in FIG. 7).

Referring again to FIG. 4, in some embodiments, one or more discrete capacitors C1-C3 can be disposed on top of and connected to one or more of the contact pads 58, 60, 62, 64 (e.g., 58, 60, and 62 as shown) and the common ground 66 so that, upon engagement of the contact pads 58, 60, 62, 64 with the connector contacts 5-8 as discussed below, an RC charging circuit can be formed for each capacitor.

Figure 8:
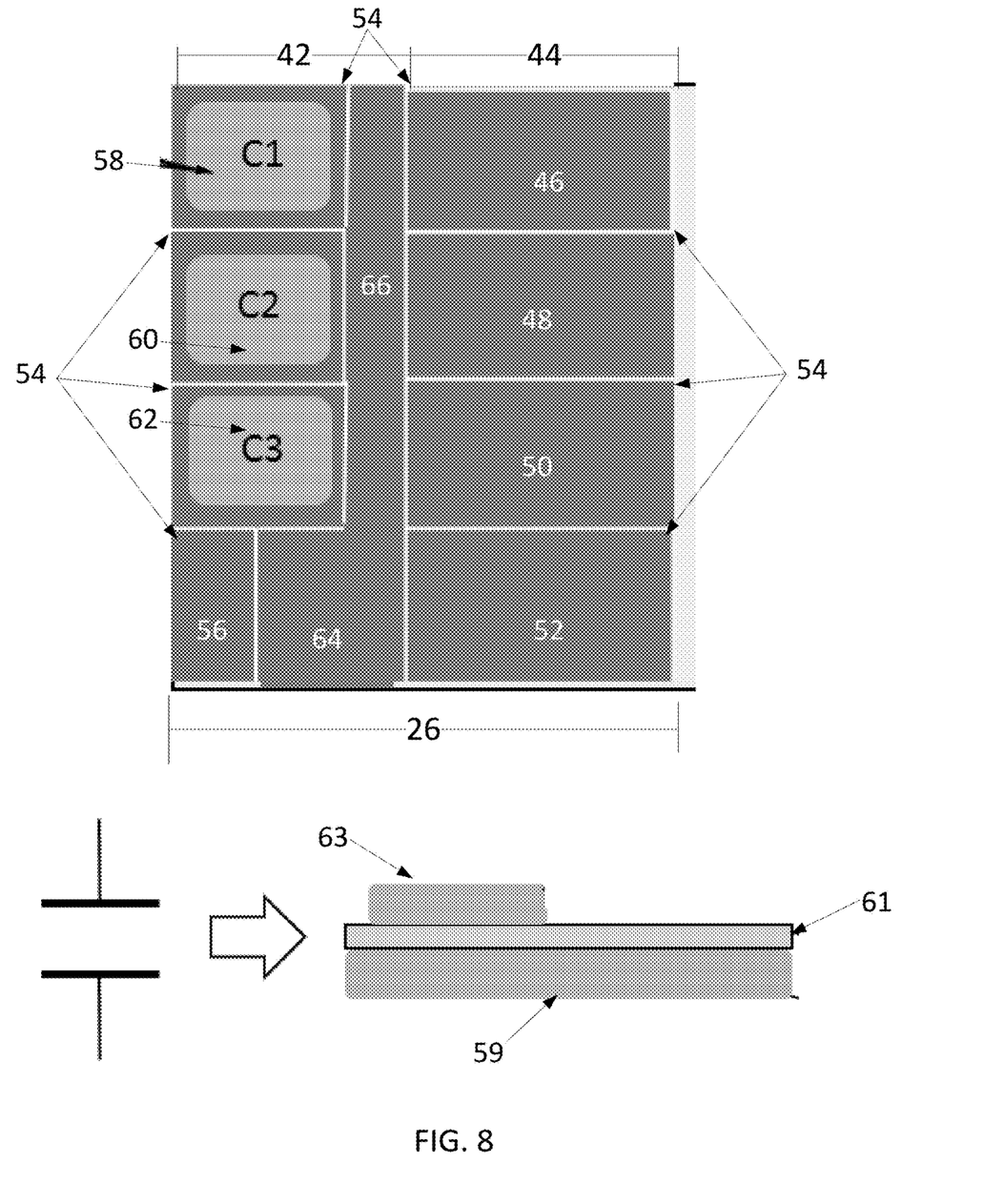
FIG. 8 is a top and side view illustrating a test strip having a distal portion including integral capacitors in accordance with various embodiments.

Referring now to FIG. 8, in some embodiments, one or more integral capacitors C1-C3 can be formed in the distal tip contact region 26. In accordance with various embodiments, the integral capacitors can be formed, for example, by forming a conductive substrate 59 (e.g., on the insulating base layer 16), forming a dielectric layer 61 on the substrate 59, and forming a conductive layer 63 on the dielectric layer 61. In accordance with some embodiments, the conductive layer 63 can also form the contact pad 58, 60, 62 for the corresponding capacitor, C1, C2, C3. Thus, the integral capacitors are integrated with the contact pads. For example, a parallel plate capacitor can be formed as part of a contact pad when the layers surrounding the dielectric layer 61 are conductive. The capacitance of such capacitors may be set to a predefined value by various known means, such as, for example, by changing the conductive area of the capacitor. In accordance with some embodiments, the conductive layer 63 can be formed by coating the dielectric layer 61 with a conductive ink.

As noted above, the conductive pattern on the base layer 16, which at least in part forms the electrical strip contacts, can be applied to the top side of the strip, the bottom side of the strip, or a combination of both. The contacting pads 58, 60, 62, 64 are configured to be operatively connected to the second plurality of connector contacts 40 within the meter connector 30. Through this operative connection, the meter can be presented with, and reads from the contacting pads, a particular code representing information signaling the meter to access data related to the underlying test strip 10. In particular, the meter is presented with a capacitive state sequence corresponding to a capacitive state of each of one or more capacitors (e.g., C1-C3 as shown in FIGS. 6A and 6B) connected to each of the contact pads 58, 60, 62, 64. FIG. 4 also illustrates the separated notch region 56. As noted, the above described conductive regions can all be formed as a result of the breaks 54 within the underlying conductive pattern of test strip 10.

Figure 5:
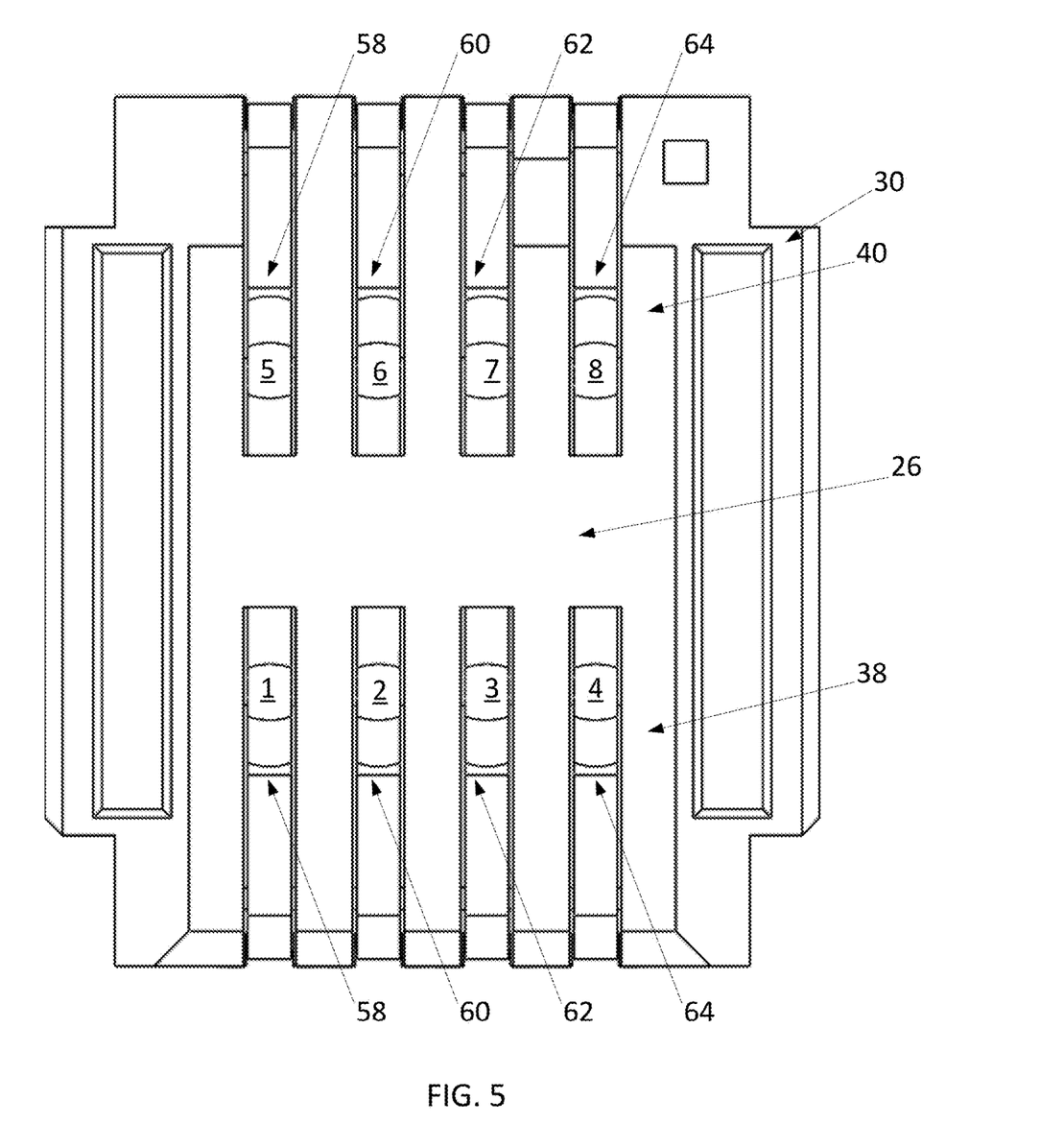
FIG. 5 is an expanded top view of a distal portion of a test strip inserted within a meter strip connector in accordance with various embodiments.

FIG. 5 illustrates the meter strip connector 30 receiving a distal strip contact region 26 of the test strip 10. FIG. 5 depicts a first plurality of connector contacts 38, labeled 1-4 respectively, and a second plurality of connector contacts 40, labeled 5-8. The connector contacts 38, 40 make contact with distinct portions of the distal strip contact region 26. In particular, upon proper insertion of the test strip 10 into the connector 30, the electrical strip contacts 46-52 are respectively electrically connected to the connector contacts 1-4, which form the first plurality of connector contacts 38. Similarly, the contacting pads 58, 60, 62, 64 are respectively electrically connected to the connector contacts 5-8, which form the second plurality of connector contacts 40.

As illustrated in FIG. 5, the first plurality of connector contacts 38 are in lateral alignment with the second plurality of connector contacts 40. However, in some embodiments, the first plurality of connector contacts 38 can be laterally staggered or offset relative to the second plurality of connector contacts 40. Additionally, although the first and second plurality of connector contacts 38, 40 are illustrated as being in distinct rows, they need not be in distinct rows and can instead be offset or arranged in any additional suitable manner, such as, for example, in distinct groups.

In some embodiments, the connection between the contacting pad 64 and the connector contact 8 can establish a common connection to ground 66 (or a voltage source where the polarity is reversed), thereby completing an electric circuit, which includes the meter and at least a portion of the conductive region 42. The completion of this circuit can perform a meter wake-up function, providing a signal to the meter to power up from low-power sleep mode.

As noted above, the contacting pads 58, 60, 62, 64 are configured to be operatively connected to the second plurality of connector contacts 40 within meter connector 30. Through this operative connection, the meter is presented with, and reads, via one or more of the contacting pads (e.g., 58, 60, 62, 64) from the capacitors C1-C3, a particular code corresponding to the capacitive state sequence, which signals the meter to access information related to a particular underlying test strip 10. The coded information can signal the meter to access data including, but not limited to, parameters indicating the particular test to be performed, parameters indicating connection to a test probe, parameters indicating connection to a check strip, calibration coefficients, temperature correction coefficients, pH level correction coefficients, hematocrit correction data, and data for recognizing a particular test strip brand.

Upon reading a particular code, an internal memory within the meter can access, through a stored microprocessor algorithm, specific calibration information (such as, for example, calibration coefficients) relating to the particular test strip. The meter can read the capacitive state sequence through, for example, an analog method such as an analog RC time constant method. In the analog mode, one or more of the second plurality of connector contacts 40 (labeled 5-8 in FIG. 5) can be connected to a pullup resistor (e.g., R1-R3) having a known resistance within the meter as shown in FIGS. 6A and 6B such that permutations of capacitive state sequences can be correlated to a distinct lot code. The capacitive state sequence can be determined, in some embodiments, by measuring a rise time for each capacitor (e.g., for each of C1, C2, and C3 as shown in FIGS. 6A and 6B) and calculating a corresponding RC time constant for each capacitor-pullup resistor pair (e.g., R1-C1, R2-C2, R3-C3 as shown in FIGS. 6A and 6B). In some embodiments, as shown in FIG. 7, for example, each capacitor can be charged for a preset duration (e.g., 01 ms as shown in FIG. 7). The capacitive state (e.g., one of 18,000 pF, 33,000 pF, 56,000 pF, 100,000 pF, or 220,000 pF as shown in FIG. 7) can then be determined from the known resistance of the pullup resistor, the known charge time, and the ratio of instantaneous capacitor voltage (V) at the expiration of the charging period to the capacitive charging voltage (Vcc) supplied by the meter. The capacitive state sequence can then be used to signal the meter to access any of the data referenced above particular to the underlying test strip.

FIG. 6A depicts a schematic diagram of the electrical connections between a meter and capacitors C1-C3 of a test strip according to various embodiments. Capacitors C1, C2, and C3 are each in a preset capacitive state, thus having a preset capacitive state sequence. Each capacitor C1-C3 is connected to the common ground 66. When the test strip 10 is fully inserted within the meter connector 30, the pullup resistors R1-R3 are electrically connected, via the connectors 58, 60, 62, in series to the capacitors C1-C3 such that each capacitor-pullup resistor pair (C1-R1, C2-R2, C3-R3 as shown) forms an RC charging circuit with the capacitive charging voltage (Vcc) supplied by the meter. The meter can then measure, via analog to digital (A/D) converters AD1, AD2, and AD3, the capacitor voltage (V) of each capacitor C1, C2, C3 during and/or after the charging period, thus permitting the meter to determine the capacitive state of each capacitor, and thus the capacitive state sequence, as described above.

In some embodiments, the A/D converters AD1, AD2, AD3 can be separate components of the meter. In some embodiments, the A/D converters AD1, AD2, AD3 can be incorporated into one or more processors of the meter, including, for example, microcontrollers, microprocessors, field-programmable gate arrays, or any other suitable processor. In some embodiments, the one or more processors can be used, for example, to access meter data, access test strip data, analyze blood chemistry, or any other suitable function to provide a blood glucose measurement to a user of the meter.

In some embodiments, charging of the capacitors C1-C3 can also prevent reuse of the test strip because the stored charge resulting from inserting the strip into the meter and charging the capacitors will inhibit a transient low pulse needed to interrupt and wake up the microcontroller while in low power mode (LPM). Thus the charged capacitors can serve as a lockout feature to prevent strip re-use. As shown in FIG. 6B, in some embodiments, in addition to the capacitors C1-C3 connected to one or more of the contact pads 58, 60, 62, a small, very high value (e.g., a resistor having a resistance of about 1M to about 10M Ohms) bleeder resistor BR1-BR3 can be connected in parallel with each capacitor to discharge any stored charge on the capacitor so that the test strip can be reinserted.

Such capacitive autocodes, by providing a plurality of capacitive states per capacitor C1-C3, permit a larger number of autocodes per connector pin (contact pad) than for a conventional system. In particular, the number of available codes is extended from the conventional $2^n-1$ codes to the $m^n$ codes of the subject patent application where n=the number of contact pads and m=the number of capacitive states. In one embodiment, if m=5 (e.g., if there are five capacitive states available for each capacitor such as one of 18,000 pF, 33,000 pF, 56,000 pF, 100,000 pF, or 220,000 pF as shown in FIG. 7), different capacitors can be installed and each connected to a contact pad, resulting in a calculable RC charging rise time for each. By calculating the RC charging rise time for one or more of the contact pads 58, 60, 62, the number of autocodes can be defined as $m^n=5^3=125$ total autocodes. Thus the number of autocodes per contact pad is significantly increased by use of the RC time constant system. In particular, the resulting number of available combinations (autocodes) increases from $2^n-1$ (i.e., each contact pad has two states for a digital binary system and an all null state cannot be used) to $m^n$, where m is the number of states per capacitor using the analog system. This would, for example, result in a three pin (contact pad) autocoding system increasing from 7 to 125 autocodes. The increase in number of autocodes on a test strip can be further seen with reference to Table 1.

TABLE 1

| # pins | # Autocodes Analog Capacitative ($m^n$) | | | # Autocodes Digital Binary ($2^n - 1$) |
|---|---|---|---|---|
| | 5 States | 4 States | 3 States | 2 States |
| 1 | 5 | 4 | 3 | 1 |
| 2 | 25 | 16 | 9 | 3 |
| 3 | 125 | 64 | 27 | 7 |
| 4 | 625 | 256 | 81 | 15 |
| 5 | 3125 | 1024 | 243 | 31 |

As shown in Table 1, a digital binary system, depending on the number of contact pads (pins), can generally provide from 1 to 31 autocodes. By contrast, the capacitive autocodes of the subject patent application, depending on the number of possible capacitive states and the number of contact pads, can generally provide from 3 to 3,125 autocodes. Thus, for test strips using a similar number of contact pads (pins), the capacitive autocoding provides a higher number of unique autocodes.

The additional information made available through this expansion of codes can include, but is not limited to, information related to hematocrit correction, information related to meter upgrades, and information related to the particular strip type. Accordingly, the use of capacitive autocodes can be used to expand the number of code configurations available with a set number of contacting pads.

It should be noted that the particular disclosed configurations of the test strip 10, and in particular the configuration of connector contacts 38, 40 and the corresponding electrical strip contacts 46, 48, 50, 52 and contact pads 58, 60, 62, 64 are merely exemplary, and different configurations can be formed without departing from the scope of the invention. For example, the underside of the test strip 10 can be formed to incorporate an additional number of contact pads in order to increase the number of contact pads (and thereby increase the amount of information and number of autocodes in the code index).

In addition to improved accuracy of measurement, the incorporation of individualized code data within individual test strips provides, for example, an ability to individually code strips so that a user no longer needs to manually enter the meter's lot code, thereby removing the possibility of user error for this critical step. Strip lot codes stored directly on individual test strips can also provide a means to ship mixed lots of strips in a single strip vial. In contrast, conventional technologies such as button/key coding require all test strips (typically packaged in a vial including 50 strips from the same lot) in a vial to be from the same lot code.

Individual strip autocodes can also permit bulk packaging because mixed lot test strips and vials including different numbers of strips are possible. Additionally, test strips from various lots can be stored in a central location and packaged for sale without the time and expense of insuring that strips are packaged from a single lot. Individual lot calibration codes stored on strips can also provide a means for varying a code across a single lot should a strip lot have variation from beginning to end or anywhere in between. Predetermined variations in manufacturing within a strip lot can be corrected by applying a continuously changing code across the lot, thereby solving yield problems and improving in-lot strip to strip variation. In addition, embedding lot codes on individual strips can be used to distinguish different types of test strips (e.g. glucose vs. ketone), check strips, or different manufacturing procedures, provide data for meter upgrades, and to correlate particular test strips for use only with a specific meter or meter type.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A test strip comprising:
   at least one electrically insulating layer;
   a conductive pattern formed on the at least one insulating layer including at least one electrode disposed on the at least one insulating layer at a proximal region of the strip, one or more electrical strip contacts disposed on the at least one insulating layer at a distal region of the test strip, conductive traces electrically connecting the electrodes to at least one of the electrical strip contacts;
   a reagent layer contacting at least a portion of at least one electrode; and
   an embedded code comprising one or more individually electrically isolated contacting pads provided distal to the electrical strip contacts, the contacting pads being associated with one of a plurality of predefined capacitive states,
   wherein the respective capacitive states associated with each of the contacting pads together form a capacitive state code such that when the test strip is inserted into a diagnostic meter the capacitive state code is read to identify data particular to the capacitive state code and the test strip, and
   wherein the capacitors are each connected to a ground.

2. The test strip of claim 1, further comprising one or more bleeder resistors each connected in parallel to one of the capacitors.

3. The test strip of claim 1, wherein each of the at least one electrodes is individually connected to one contact of the electrical strip contacts.

4. The test strip of claim 1, wherein the electrical strip contacts and the contacting pads are positioned to form distinct groups of electrical contacts, the groups being spaced from one another.

5. The test strip of claim 1, wherein at least one of the capacitive states is different than at least one other capacitive state.

6. The test strip of claim 1, wherein an electrically insulating region separates the electrical strip contacts from the contacting pads.

7. The test strip of claim 1, wherein the contacting pads are configured for contact, when inserted into a compatible meter, with a plurality of contacts in a corresponding connector of the meter.

8. The test strip of claim 7, wherein each one of the plurality of contacts in the corresponding connector of the meter is connected to one or more pull up resistors.

9. The test strip of claim 1, wherein an additional conductive pattern is formed on the insulating layer on a side opposite from that including the electrical strip contacts, the additional conductive pattern comprising a second plurality of electrical strip contacts and at least one additional contact pad electrically connected to one or more capacitors configured in one of the plurality of predefined capacitive states to form a second capacitive state code to identify additional data particular to the test strip.

10. The test strip of claim 4, wherein the electrical strip contacts and the contacting pads are positioned to form first and second distinct rows of contacts.

11. The test strip of claim 9, wherein the first and second rows of contacts are laterally staggered relative to each other.

12. The test strip of claim 1, wherein the ground is positioned proximal to the contact pads and distal to the electrical strip contacts.

13. A method of making a plurality of test strips, the method comprising:
    forming a plurality of test strip structures on one sheet, each of the test strip structures including:
        an electrically insulating layer;
        a conductive pattern formed on the at least one insulating layer including at least one electrode disposed on the at least one insulating layer at a proximal region of the strip, one or more electrical strip contacts disposed on the at least one insulating layer at a distal region of the test strip, conductive traces electrically connecting the electrodes to at least one of the electrical strip contacts;
        a reagent layer contacting at least a portion of at least one electrode;
        an embedded code comprising one or more individually electrically isolated contacting pads provided distal to the electrical strip contacts, the contacting pads being associated with one of a plurality of predefined capacitive states, wherein the respective capacitive states associated with each of the contacting pads together form a capacitive state code such that when the test strip is inserted into a diagnostic meter the capacitive state code is read to identify data particular to the capacitive state code and the test strip;
        an additional conductive pattern formed on the insulating layer on a side opposite from that including the electrical strip contacts, the additional conductive pattern comprising a second plurality of electrical strip contacts and at least one additional contact pad electrically connected to one or more capacitors configured in one of the plurality of predefined capacitive states to form a second capacitive state code to identify additional data particular to the test strip; and
    separating the test strip structures into the plurality of test strips.

14. The method of claim 13, the test strip further comprising a reagent layer contacting at least a portion of at least one electrode.

15. The method of claim 13, wherein at least one of the capacitive states is different than at least one other capacitive state.

16. A test strip comprising:
    at least one electrically insulating layer;
    a conductive pattern formed on the at least one insulating layer including at least one electrode disposed on the at least one insulating layer at a proximal region of the strip, one or more electrical strip contacts disposed on the at least one insulating layer at a distal region of the test strip, conductive traces electrically connecting the electrodes to at least one of the electrical strip contacts;
    a reagent layer contacting at least a portion of at least one electrode;
    an embedded code comprising one or more individually electrically isolated contacting pads provided distal to the electrical strip contacts, the contacting pads being associated with one of a plurality of predefined capacitive states; and
    one or more bleeder resistors each connected in parallel to one of the capacitors,
    wherein the respective capacitive states associated with each of the contacting pads together form a capacitive state code such that when the test strip is inserted into a diagnostic meter the capacitive state code is read to identify data particular to the capacitive state code and the test strip.

17. A test strip comprising:
    at least one electrically insulating layer;
    a conductive pattern formed on the at least one insulating layer including at least one electrode disposed on the at least one insulating layer at a proximal region of the strip, one or more electrical strip contacts disposed on the at least one insulating layer at a distal region of the test strip, conductive traces electrically connecting the electrodes to at least one of the electrical strip contacts;
    a reagent layer contacting at least a portion of at least one electrode; and
    an embedded code comprising one or more individually electrically isolated contacting pads provided distal to the electrical strip contacts, the contacting pads being associated with one of a plurality of predefined capacitive states,
    wherein the respective capacitive states associated with each of the contact pads together form a capacity state code such that when the test strip is inserted into a diagnostic meter the capacitive state code is read to identify data particular to the capacitive state code and the test strip;
    wherein an additional conductive pattern is formed on the insulating layer on a side opposite from that including the electrical strip contacts, the additional conductive pattern comprising a second plurality of electrical strip contacts and at least one additional contact pad electrically connected to one or more capacitors configured in one of the plurality of predefined capacitive states to form a second capacitive state code to identify additional data particular to the test strip.

18. The test strip of claim 17, wherein the first and second rows of contacts are laterally staggered relative to each other.

* * * * *